United States Patent
Al-Ofi et al.

(10) Patent No.: US 11,493,465 B2
(45) Date of Patent: Nov. 8, 2022

(54) MULTI-FREQUENCY DIELECTRIC COAXIAL PROBE FOR FORMATION ANALYSIS

(71) Applicants: Salah Al-Ofi, Khobar (SA); Hasan Kesserwan, Al-Khobar (SA); Guodong Jin, Katy, TX (US)

(72) Inventors: Salah Al-Ofi, Khobar (SA); Hasan Kesserwan, Al-Khobar (SA); Guodong Jin, Katy, TX (US)

(73) Assignee: BAKER HUGHES OILFIELD OPERATIONS LLC, Houston, TX (US)

( * ) Notice: Subject to any disclaimer, the term of this patent is extended or adjusted under 35 U.S.C. 154(b) by 194 days.

(21) Appl. No.: 17/084,791

(22) Filed: Oct. 30, 2020

(65) Prior Publication Data
US 2021/0131988 A1    May 6, 2021

Related U.S. Application Data

(60) Provisional application No. 62/928,631, filed on Oct. 31, 2019.

(51) Int. Cl.
*G01N 15/08* (2006.01)
*G01N 27/02* (2006.01)

(52) U.S. Cl.
CPC .................. *G01N 27/026* (2013.01)

(58) Field of Classification Search
CPC ........... G01N 33/2823; G01N 33/2847; G01N 27/221; G01N 22/00; G01N 27/02; G01N 22/04; G01N 33/18; G01N 27/026
See application file for complete search history.

(56) References Cited

U.S. PATENT DOCUMENTS

| | | | |
|---|---|---|---|
| 4,396,062 A | 8/1983 | Iskander | |
| 8,602,128 B2 | 12/2013 | Ligneul et al. | |
| 2012/0273273 A1* | 11/2012 | Ligneul | G01N 33/24 175/46 |
| 2014/0028318 A1 | 1/2014 | Badri et al. | |
| 2018/0321412 A1 | 11/2018 | Wang et al. | |
| 2018/0356356 A1* | 12/2018 | Black | G01N 33/2847 |
| 2019/0017952 A1* | 1/2019 | Noel | G01R 27/2617 |

OTHER PUBLICATIONS

Kesserwan et al., "Porosity Measurements on Drill Cuttings—Comprehensive Inputs to Formation Evaluation near Real-Time While Drilling", SPE-188881-MS, 2017, pp. 1-9.

(Continued)

*Primary Examiner* — Alesa Allgood
(74) *Attorney, Agent, or Firm* — Cantor Colburn LLP

(57) ABSTRACT

Systems and methods to evaluate a formation by analyzing drill cuttings involve a multi-frequency dielectric coaxial probe to obtain a reflected voltage from a medium under test based on a reference voltage over a frequency range. The medium under test includes the drill cuttings. The system includes a processor to compute an effective permittivity of the drill cuttings over the frequency range based on a reflection coefficient, which is a ratio of the reflected voltage to the reference voltage over the frequency range, and to determine one or more parameters from the effective permittivity. The one or more parameters are used to make decisions about subsequent drilling in the formation.

20 Claims, 4 Drawing Sheets

OTHER PUBLICATIONS

Baker-Jarvis et al., "Analysis of an Open-Ended Coaxial Probe with Lift-Off for Nondestructive Testing", IEEE Transactions on Instrumentation and Measurement, vol. 43, No. 5, Oct. 1994, pp. 711-718.
Birchak et al., "High Dielectric Constant Microwave Probes for Sensing Soil Moisture", Proceedings of the IEEE, vol. 62, No. 1, Jan. 1974, pp. 93-98.
Egermann et al., "A Fast and Direct Method of Permeability Measurements on Drill Cuttings", SPE 77563, 2002, pp. 1-8.
Esteban et al., "Insights of dielectric measurements from cuttings recovered along the deepest offshore well int he world (Nankai trough accretionary prism): IPDP expedition 338, site C0002F", 24 International Geophysical Conference and Exhibition, Feb. 2015, pp. 1-6.
Marsala et al., "Transient method implemented under Unsteady-State conditions for Low and very Low Permeability measurements on Cuttings", SPE/ISRM 47202, 1998, pp. 1-7.
Revil, A. "Effective conductivity and permittivity of unsaturated porous materials in the frequency range 1 mHz-1GHz", Water Resources Research, vol. 49, 2013, pp. 306-327.
Saasen et al., "Automatic Measurement of Drilling Fluid and Drill Cuttings Properties", IADC/SPE 112687, pp. 2008, pp. 1-17.
Santarelli et al., "Formation Evaluation From Logging on Cuttings", SPE Reservoir Evaluation & Engineering, Jun. 1998, pp. 238-244.
Siddiqui et al., "Techniques for Extracting Reliable Density and Porosity Data From Cuttings", SPE 96918, 2005, pp. 1-13.
Stroud et al., "Analytical model for the dielectric response of brine-saturated rocks", Physical Review B, vol. 34, No. 8, Oct. 15, 1986, pp. 5145-5153.
Stuchly et al., "Coaxial Line Reflection Methods for Measuring Dielectric Properties of Biological Substances at Radio and Microwave Frequencies—A Review", IEEE Transactions on Instrumentation and Measurement, vol. IM-29, No. 3, Sep. 1980, pp. 176-183.
Internationl Preliminary Report on Patentability for PCT Application No. PCT/US2020/058180, dated May 12, 2022, pp. 1-6.

\* cited by examiner

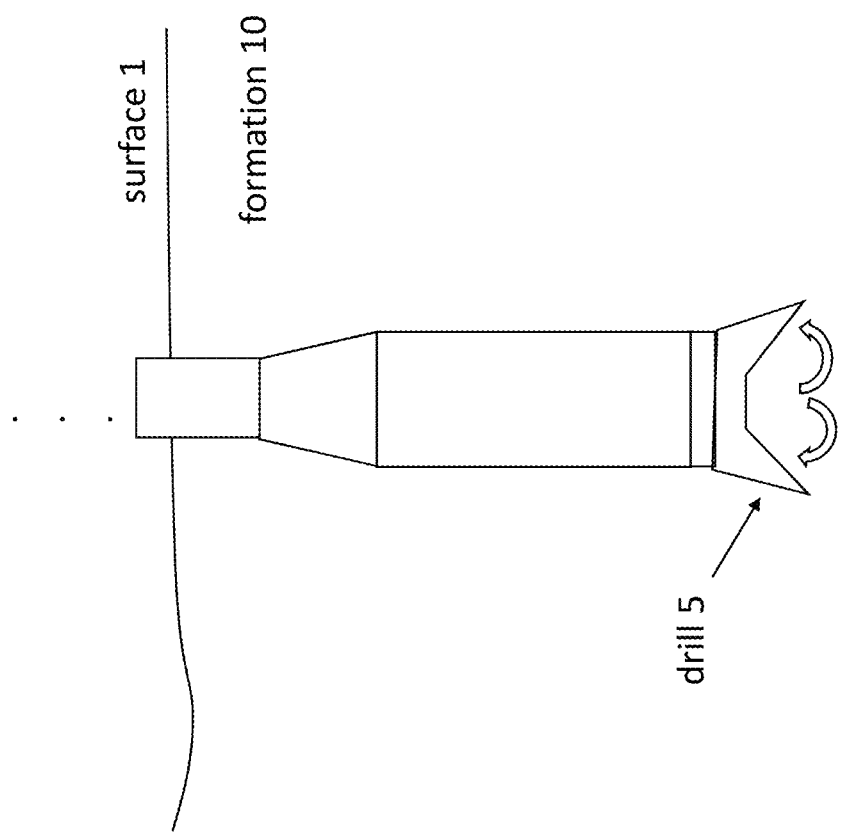

MULTI-FREQUENCY DIELECTRIC COAXIAL PROBE FOR FORMATION ANALYSIS

CROSS-REFERENCE TO RELATED APPLICATIONS

This application claims the benefit of U.S. Provisional Application No. 62/928,631 filed Oct. 31, 2019, the disclosure of which is incorporated herein by reference in its entirety.

BACKGROUND

In the resource recovery industry, information about a formation (i.e., the rock that is drilled through) can affect decisions about drilling and production. During the drilling process, rock samples are produced as drill cuttings. The drill cuttings from different sections of the borehole can provide information about the different types of formations that are encountered during drilling. Analysis of the drill cuttings represents a quick and continuous analysis technique when compared with wireline logging, for example, which requires introducing tools into the borehole. Prior analysis of drill cuttings required extensive and careful treatment of the cuttings or specific particle sizes. Thus, the industry would benefit from a multi-frequency dielectric coaxial probe for formation analysis.

BRIEF DESCRIPTION OF THE DRAWINGS

The following descriptions should not be considered limiting in any way. With reference to the accompanying drawings, like elements are numbered alike:

FIG. 5 is a block diagram of aspects of a system that generates the cuttings that are analyzed by the probe according to one or more embodiments of the invention.

DETAILED DESCRIPTION

A detailed description of one or more embodiments of the disclosed apparatus and method are presented herein by way of exemplification and not limitation with reference to the Figures.

As previously noted, analysis of drill cuttings offers a quick approach to formation evaluation without the need for specialized downhole tools. Prior analysis of drill cuttings required treatment and sizing of the cuttings. Dielectric spectroscopy techniques require less treatment of the cuttings. According to one or more embodiments of the invention, a multi-frequency dielectric coaxial probe is used for formation analysis. Specifically, drill cuttings are put in a host fluid to form a medium under test (MUT). A multi-frequency dielectric coaxial probe is lowered into the MUT, and a voltage is applied at different frequencies. The resulting reflected voltage is measured and operated on to determine different characteristics that indicate formation properties. The comparison of results obtained using different host fluids provides additional insights, as detailed.

Figure 1:
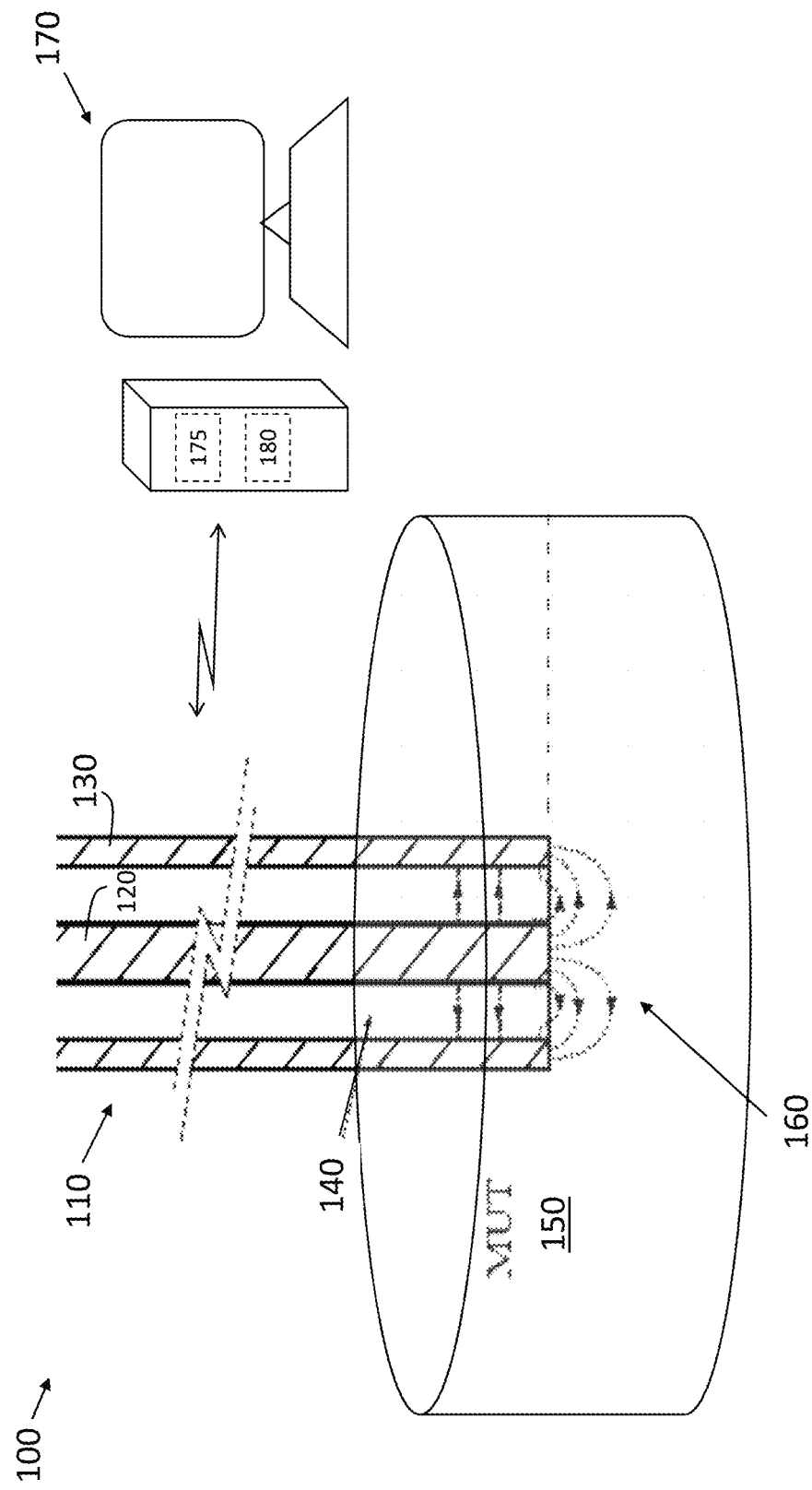
FIG. 1 depicts a system that includes a multi-frequency dielectric coaxial probe for formation analysis according to one or more embodiments of the invention.

Referring to FIG. 1, a system 100 that includes a multi-frequency dielectric coaxial probe 110 for formation analysis according to one or more embodiments of the invention is shown. The probe 110 includes an inner conductor 120 and an outer conductor 130 that are separated by a dielectric material 140. The dielectric material 140 may be teflon or glass, for example. The probe 110 is calibrated with known standard terminations to cancel the effect of the probe length and connections. The probe 110 is partially immersed in a MUT 150, as shown. The MUT 150 is further discussed with reference to FIGS. 2 and 3. According to one or more embodiments of the invention, a voltage at different frequencies is applied between the inner conductor 120 and the outer conductor 130 of the probe (i.e., at the dielectric material 140). The frequencies may range from 10 megahertz (MHz) to 10 gigahertz (GHz). The greater the number of frequencies within the range, the greater the granularity of the results discussed with reference to FIG. 4.

A reflected voltage is measured by the probe 110. The probe 110 is excited by a reference voltage at one frequency at a time. The reference voltage generates a transverse electromagnetic wave (TEM) in the dielectric material 140. At the interface between the probe 110 and the MUT 150, two waves, generally indicated as 160, are generated as the reference wave. One is a transmitted wave into the MUT 150 and the other is a reflected wave back to the probe 110. The reflected wave has a voltage that is measured by the probe 110. This reflected voltage has a similar frequency as the reference voltage that generates the reference wave, but its magnitude is attenuated and it is time delayed. The ratio of the reflected voltage to the reference voltage is the reflection coefficient. The reflection coefficient is then provided to a processing system 170 for processing, as detailed herein. The processing system 170 includes one or more memory devices 175 and one or more processors 180 to perform the analysis. The memory device 175 may store measurements of reflected voltage and instructions for processing the measurements that are executed by the processor 180.

Generally, the parameters of interest with regard to the formation 10 (FIG. 5) are water saturation (i.e., amount of water 235 in pores 230 of cuttings 220 (FIG. 2)), wettability (i.e., type of fluid formed as a film 310 (FIG. 3) or in pores 230 of the cuttings 220), porosity (i.e., void spaces or pores 230 within the cuttings 220), and salinity of water 235 in the pores 230 (i.e., concentration of free salt ions in the water 235 of the pores 230). These parameters are obtained based on a determination of the effective permittivity (i.e., dielectric constant) of the MUT 150. Permittivity and dielectric constant are used interchangeably herein.

The permittivity of a given medium is the amount of energy stored or dissipated per unit volume as an electric field passes through the medium. This permittivity or dielectric constant is expressed as a complex number $\varepsilon^*$:

$$\varepsilon^* = \varepsilon'(\omega) + i\varepsilon''(\omega) = \varepsilon'(\omega) + i\frac{\sigma(\omega)}{\omega\varepsilon_0} \qquad [\text{Eq. 1}]$$

In EQ. 1, $\varepsilon'$ is the real component of dielectric constant, $\varepsilon''$ is the imaginary component of dielectric constant, $\omega$ is the angular frequency in radians/second, $\sigma$ is the conductivity in Siemens/meters (m), $\varepsilon_0$ and is the free-space dielectric constant which is $8.85 \times 10^{-12}$ Farads/m². The dielectric constant is a function of frequency. In the MHz range, the dielectric constant is dominated by interfacial polarization, which occurs between any interface with a contrast in permittivity (e.g., between the cuttings 220 and host fluid 210 (FIG. 2)). In the GHz range, the orientational polarization dominates and occurs at a molecular scale.

The reflection coefficient measured by the probe 110 is used to compute the dielectric constant (i.e., permittivity) of the MUT 150 using a full-wave electromagnetic model. This is a known computation that is not detailed herein. Based on the known computation, the permittivity computed from the measured reflection coefficient is referred to as effective permittivity herein. For a heterogeneous mixture such as the cuttings 220 suspended in the host fluid 210, a mixing model is used to determine physical parameters (e.g., volumetric concentration of each constituent of the MUT 150) from the measured effective permittivity. For a porous medium such as the cuttings 220 partially saturated by a host fluid 210 such as water or oil, a complex refractive index model (CRIM) is expressed as:

$$\sqrt{\varepsilon_{CRIM}} = \emptyset S_w \sqrt{\varepsilon_w} + \emptyset (1-S_w)\sqrt{\varepsilon_{oil}} + (1-\emptyset)\sqrt{\varepsilon_m} \quad [\text{EQ. 2}]$$

In EQ. 2, $\varepsilon_{CRIM}$ is the effective dielectric constant of the MUT 150, $\varepsilon_w$ is the permittivity of water (i.e., all water, whether in the pores 230 or host fluid 210 (FIG. 2)), $\varepsilon_{oil}$ is the permittivity of oil (i.e., all oil, whether in the pores 230 or host fluid 210), $\varepsilon_m$ is the solid matrix or grains permittivity (i.e., solid part of the cuttings 220), $\emptyset$ is the porosity of the medium, and $S_w$ is the water saturation of the MUT 150.

Figure 2:
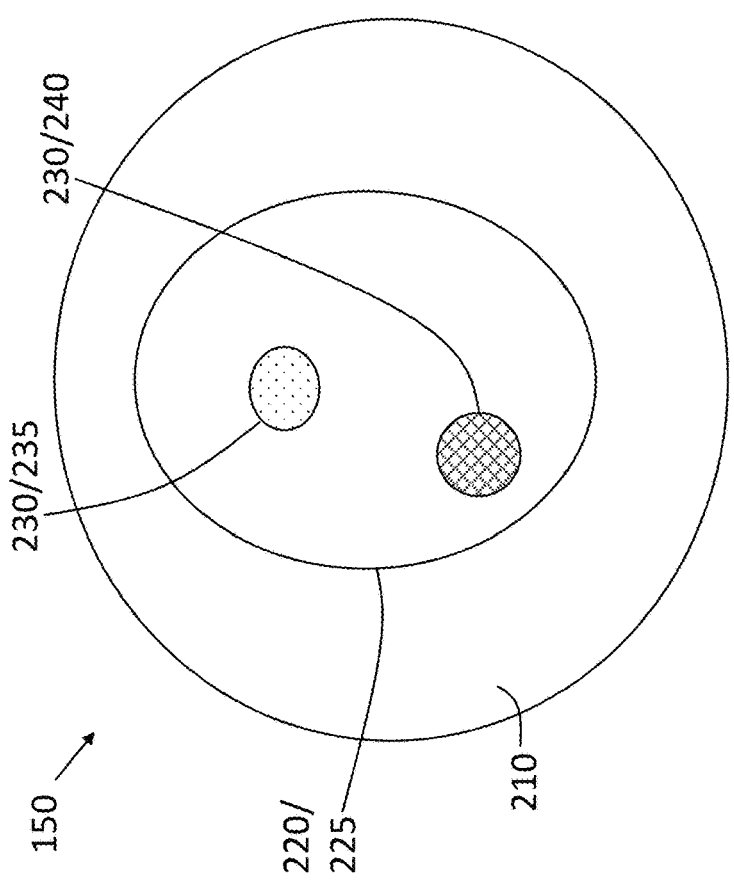
FIG. 2 is a cross-sectional view of aspects of an exemplary medium under test that is analyzed by the probe according to one or more embodiments of the invention.

The CRIM is a volumetric-based mixing model and describes molecular polarization, which occurs in the GHz range. Other models that capture information about the geometry of the constituents of the MUT 150 may be used to describe the interfacial polarization, which occurs in the MHz range, and to solve for effective cementation factor m, which describes the connectivity or tortuosity of the water 235 in pores 230 of the cuttings 220 (FIG. 2). To derive parameters of interest such as water saturation of the cuttings 220 $S_{wc}$ or surface wettability index of the cuttings 220 $WI_c$, effective permittivity computations, which are based on reflection coefficient measurements, are used with an appropriate mixing model and with host fluids 210 with different permittivity characteristics. This is further detailed with reference to FIGS. 2 and 3.

Figure 3:
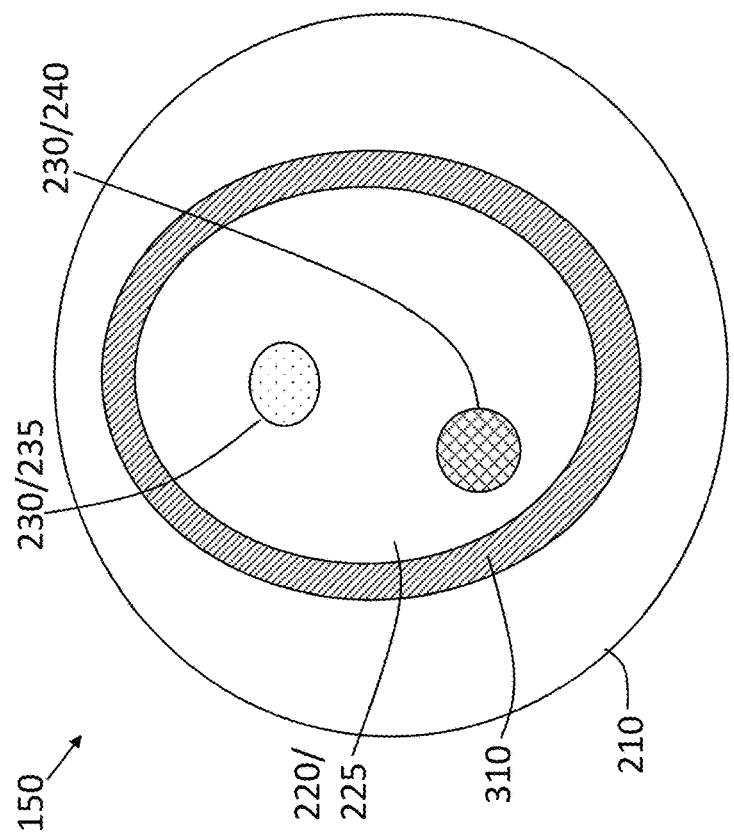
FIG. 3 is a cross-sectional view of aspects of another exemplary medium under test that is analyzed by the probe according to one or more embodiments of the invention.

FIG. 2 is a cross-sectional view of aspects of an exemplary MUT 150 analyzed by the probe 110 according to one or more embodiments of the invention. The MUT 150 is a mix of cuttings 220, which are the crystals or grains obtained from the drilling, immersed in host fluid 210. The cuttings 220 include the solid portion or matrix 225 and are shown with pores 230 that are filled with water 235 or oil 240. FIG. 2 illustrates an exemplary MUT 150 that results from an assumption that the cuttings 220 are coated with non-conductive fluid (e.g., oil) and the host fluid 210 is also non-conductive fluid. That is, the discussion with reference to FIG. 2 does not consider the cuttings 220 to include a film 310 (FIG. 3).

As such, the exemplary MUT 150 of FIG. 2 facilitates a simplified approach to reducing EQ. 2 to only three unknowns, the porosity $\emptyset$, water saturation of the cuttings 220 $S_{wc}$, and the permittivity of the matrix 225 of the cuttings 220 $\varepsilon_m$. It is assumed that permittivity of water 235 $\varepsilon_w$ and permittivity of oil 240 $\varepsilon_{oil}$ are already known. Water 235 permittivity $\varepsilon_w$ is dependent on salinity, temperature, and pressure. Thus, if those three parameters are known, water 235 permittivity $\varepsilon_w$ can be determined from known models.

Four systems of measurements, to allow for solving four unknowns in EQ. 3 below, can be obtained by changing the host fluid 210 and, for example, a temperature of the host fluid 210 and by adding a term corresponding to inter-cutting porosity, $\emptyset_h$ (i.e., porosity of the host fluid 210) while considering the porosity $\emptyset$ as the porosity of each cutting 220. Then, EQ. 2 becomes:

$$\frac{\sqrt{\varepsilon_{CRIM}} = \emptyset_h \sqrt{\varepsilon_h} + \emptyset S_{wc}\sqrt{\varepsilon_w} + \emptyset(1-S_{wc})\sqrt{\varepsilon_{oil}} + (1-\emptyset-\emptyset_h)}{\sqrt{\varepsilon_m}} \quad [\text{EQ. 3}]$$

In EQ. 3, $\varepsilon_h$ is the known permittivity of the host fluid 210. The four unknowns are porosity $\emptyset$, water saturation of the cuttings 220 $S_{wc}$, and the permittivity of the matrix 225 of the cuttings 220 $\varepsilon_m$, as noted previously, and additionally the permittivity of the host fluid 210 $\varepsilon_h$. The host fluid 210 can be one of the fluids (e.g., water, oil) that is inside the pores 230 of the cuttings 220 but with a different temperature or may be another fluid with known permittivity such as acetone or methanol.

FIG. 3 is a cross-sectional view of aspects of another exemplary MUT 150 analyzed by the probe 110 according to one or more embodiments of the invention. In FIG. 3, the cutting 220 includes a film 310 of a fluid surrounding the cutting 220. Exemplary films 310 include water and oil. By forming different MUT 150 using different host fluids 210, an MUT 150 with a film 310 that contrasts with the host fluid 210 (e.g., water film 310 in oil host fluid 210), another approach may be used to evaluate the formation 10 (FIG. 5). Evaluation of the film 310 around the cuttings 220 can be used to determine the wetting conditions of the cuttings 220 or the surface wettability index of the cuttings 220 $WI_c$. According to an exemplary embodiment, only the fluids in the pores 230 of the cuttings 220 are used as host fluids 210.

A cutoff frequency ($f_c$) (e.g., 100 MHz) indicates the frequency at which the molecular polarization starts to dominate interfacial polarization in multi-frequency dielectric measurements. That is, molecular polarization occurs on the entire frequency scale while interfacial polarization occurs only at lower frequency ranges and decays with increasing frequency. At the cutoff frequency $f_c$, the decay is such that the molecular polarization dominates. A more specific cutoff frequency $f_c$ value can be determined experimentally based on pore structure and shape, for example. The degree of interfacial polarization, which occurs at frequencies below $f_c$, is determined based on the amount and shape of interfaces between two different constitutes of the pores 230 of the cuttings 220, while the degree of molecular polarization, which occurs at frequencies above $f_c$, is governed by the volume of bulk constitutes (e.g., total volume of water 235 in pores 230 and in host fluid 210 or oil 240 in pores 230 and in host fluid 210).

When the film 310 around cuttings 220 is water, an oil host fluid 210 will result in a high number of interfaces between the water film 310 and oil host fluid 210 and between the water film 310 and oil 240 in the pores 230. Thus, the low-frequency dielectric measurement (i.e., effective permittivity) is relatively higher than the high-frequency measurement when the cuttings 220 with a water film 310 are put in a host fluid 210 of oil. When cuttings 220 with a water film 310 are put in a host fluid 210 of water, the effective permittivity determined using the probe 110 will be increased, relative to the effective permittivity using a host fluid 210 of oil, due the enhancement of molecular polarization, which occurs over the entire frequency range as previously noted. That is, effective permittivity is higher at lower frequencies with both host fluids 210 but is relatively higher for a water host fluid 210 than oil. This is illustrated in graph set 410 (FIG. 4).

When the film 310 around the cuttings 220 is oil, there are fewer water interfaces when the cuttings 220 are immersed in a host fluid 210 of oil. Thus, a flatter dielectric dispersion response results (i.e., the effective permittivity is essentially a flat line). However, when the film 310 around the cuttings 220 is oil and the cuttings 220 are immersed in a host fluid 210 that is water, the amount of water interfaces (between the host fluid 210 and pores 230 with water 235) will increase the low frequency dielectric response (i.e., the effective permittivity will be higher at lower frequencies). This is illustrated in graph set 420 (FIG. 4). These differences based on the different host fluids 210 can be used to determine the wetting condition (i.e., whether the film 310 is water or oil), as further discussed with reference to FIG. 4.

Figure 4:
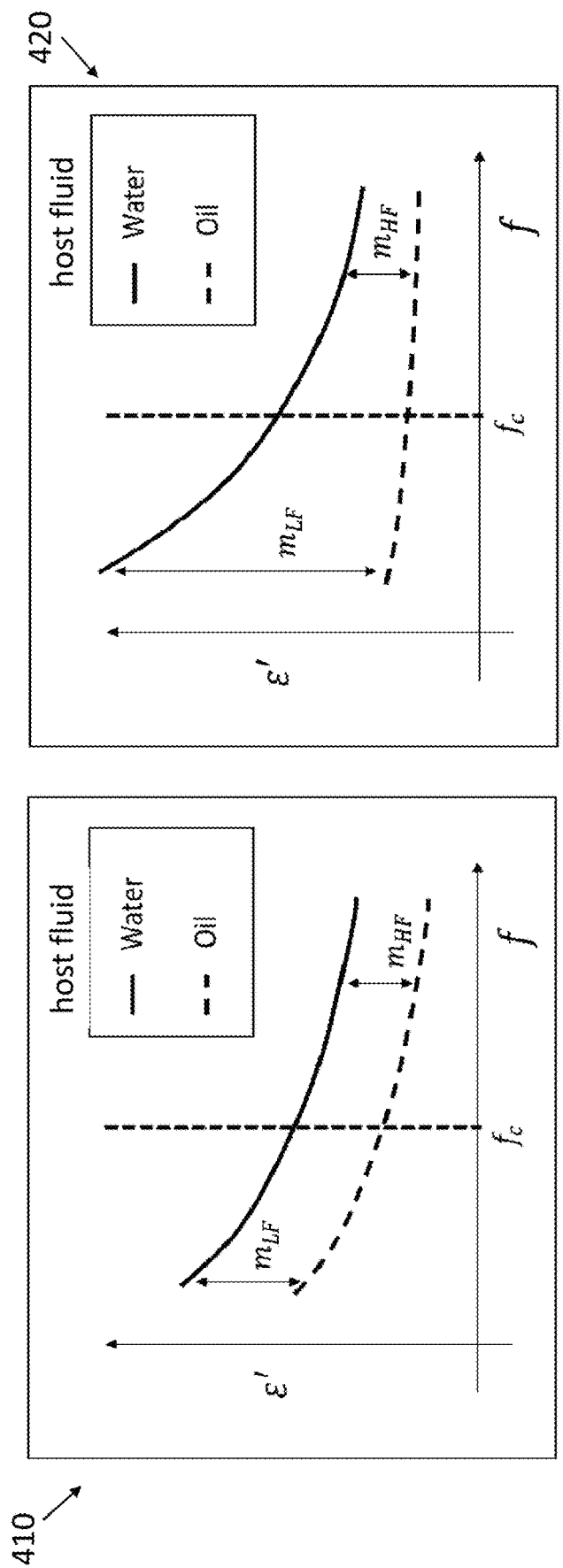
FIG. 4 illustrates permittivity results obtained using the probe according to one or more embodiments.

FIG. 4 illustrates permittivity results obtained using the probe 110 according to one or more embodiments. Two graph sets 410 and 420 are shown. Real permittivity $\varepsilon'$ and frequency f are indicated on perpendicular axes in both graph sets 410, 420, with the cutoff frequency $f_c$ shown. In graph set 410, the cuttings 220 have a film 310 of water, the real permittivity $\varepsilon'$ is shown with a solid line for a host fluid 210 of water, and the real permittivity $\varepsilon'$ is shown with a dashed line for a host fluid 210 of oil. In graph set 420, the cuttings 220 have a film 310 of oil, the real permittivity $\varepsilon'$ is shown with a solid line for a host fluid 210 of water, and the real permittivity $\varepsilon'$ is shown with a dashed line for a host fluid 210 of oil. In each graph set 410, 420, the difference in real permittivity $\varepsilon'$ at a low frequency ($f<f_c$) is indicated as $m_{LF}$, and the difference in real permittivity $\varepsilon'$ at a high frequency ($f>f_c$) is indicated as $m_{HF}$. The ratio $m_{LF}/m_{HF}$ provides the wettability of the cuttings 220. As graph set 410 indicates, the ratio $m_{LF}/m_{HF}$ is ≤1, and, as graph set 420 indicates, the ratio $m_{LF}/m_{HF}$ is >>1. As previously discussed, the composition of the film 310 and the host fluid 210 leads to the resulting graphs sets 410,420 and ratios $m_{LF}/m_{HF}$.

A more comprehensive approach to evaluating both the water saturation and wettability of cuttings 220 includes using a different mathematical representation for the cuttings 220, which considers the solid matrix 225 of the cuttings 220, the film 310, and water 235 or oil 240 in the pores 230 as a whole, and which separates the porosity $\varnothing_c$ and water saturation of the cuttings 220 $S_{wc}$ from porosity $\varnothing_h$ and water saturation of the host fluid 210 $S_{wh}$. The permittivity of the cuttings 220 can be substituted for another mixing model as a modified matrix permittivity $\varepsilon_{m'}$ given by:

$$\sqrt{\varepsilon_{m'}} = \varnothing_c S_{wc}\sqrt{\varepsilon_{wc}} + \varnothing_c(1-S_{wc})\sqrt{\varepsilon_{oc}} + (1-\varnothing_c)\sqrt{\varepsilon_m} \quad [\text{EQ. 4}]$$

In EQ. 4, $\varepsilon_{wc}$ and $\varepsilon_{oc}$ are the permittivity of water 235 and oil 240 in the pores 230 of the cuttings 220.

By substituting the expression in EQ. 4 defining $\varepsilon_{m'}$ for $\varepsilon_m$ in EQ. 2, the following results:

$$\sqrt{\varepsilon_{CRIM}} = \varnothing_h S_{wh}\sqrt{\varepsilon_{wh}} + \varnothing_h(1-S_{wh})\sqrt{\varepsilon_{oh}} + (1-\varnothing_h)[\varnothing_c S_{wc}\sqrt{\varepsilon_{wc}} + \varnothing_c(1-S_{wc})\sqrt{\varepsilon_{oc}} + (1-\varnothing_c)\sqrt{\varepsilon_m}] \quad [\text{EQ. 5}]$$

In EQ. 5, $\varnothing_h$ and $S_{wh}$ are the porosity and water saturation of the host fluid 210. With a system of five independent effective permittivity measurements for a given MUT 150, the five unknowns in EQ. 5 can be solved. As previously noted, each of the independent systems may be based on a difference in host fluid 210 or temperature of the host fluid 210, for example. The five unknowns are the porosity $\varnothing_h$ and water saturation $S_{wh}$ of the host fluid 210, porosity of the cuttings 220 $\varnothing_c$, water saturation of the cuttings 220 $S_{wc}$, and permittivity of the matrix 225 $\varepsilon_m$.

It is assumed that the permittivity of the host fluid 210 (e.g., $\varepsilon_{wh}$ or $\varepsilon_{oh}$), and the permittivity of the water 235 $\varepsilon_{wc}$ and oil 240 $\varepsilon_{oc}$ in the pores 230 of the cuttings 220 are known. The water saturation of the host fluid 210 $S_{wh}$ can be used as a metric to indicate the wettability of the cuttings 220. That is, if $S_{wh}>0$ and the host fluid 210 is oil, then the cuttings 220 must be water-wet (i.e., film 310 is water), and if $S_{wh}<1$ and the host fluid 210 is water, then the cuttings 220 must be more oil-wet (i.e., film 310 of oil). The value of the water saturation of the host fluid 210 $S_{wh}$ in the previously discussed embodiments can be used as a quantitative measure of the wettability of the cuttings 220. If a mineralogy assessment or other source provides the permittivity of the matrix 225 $\varepsilon_m$, then the number of unknowns in EQ. 5 can be reduced from five to four.

FIG. 5 is a block diagram of aspects of a system that generates the cuttings 220 analyzed by the probe 110 according to one or more embodiments of the invention. A drill 5 is shown below a surface 1 (e.g., below the surface of the earth) in a formation 10. The drill 5 generates the cuttings 220 as it moves through the formation 10. By analyzing the cuttings 220 as discussed herein, decisions can be made about the direction and depth of drilling, for example. For example, reservoir volume and producibility (i.e., how well a resource, such as oil, may be recovered) can be determined based on the porosity, water saturation, and wettability of the cuttings 220. Thus, decisions about whether to continue the resource recovery effort in the formation 10 may be made according to the formation evaluation via analysis of the drill cuttings 220.

Set forth below are some embodiments of the foregoing disclosure:

Embodiment 1

A system to evaluate a formation by analyzing drill cuttings, the system comprising: a multi-frequency dielectric coaxial probe configured to obtain a reflected voltage from a medium under test based on a reference voltage over a frequency range, the medium under test including the drill cuttings; and a processor configured to compute an effective permittivity of the drill cuttings over the frequency range based on a reflection coefficient, which is a ratio of the reflected voltage to the reference voltage over the frequency range, and to determine one or more parameters from the effective permittivity, wherein the one or more parameters are used to make decisions about subsequent drilling in the formation.

Embodiment 2

The system as in any prior embodiment, wherein the medium under test also includes a host fluid.

Embodiment 3

The system as in any prior embodiment, wherein the processor is further configured to determine the effective permittivity over the frequency range, using water as the host fluid, as a first data set, to determine the effective permittivity over the frequency range, using oil as the host fluid, as a second data set, to determine a difference between a value of the effective permittivity in the first data set and in the second data set at a frequency below a cutoff frequency $f_c$ as $m_{LF}$, and to determine a difference between a value of the effective permittivity in the first data set and in the second data set at a frequency above the cutoff frequency $f_c$ as $m_{HF}$.

Embodiment 4

The system as in any prior embodiment, wherein the processor is configured to determine that a film on the drill cuttings is water based on $m_{LF}/m_{HF}$ being ≤1 and to determine that the film on the drill cuttings is oil based on $m_{LF}/m_{HF}$ being >>1.

Embodiment 5

The system as in any prior embodiment, wherein the processor is configured to use a complex refractive index model (CRIM) mixing model with the effective permittivity to obtain a representation:

$$\sqrt{\varepsilon_{CRIM}} = \emptyset_h S_{wh}\sqrt{\varepsilon_{wh}} + \emptyset_h(1-S_{wh})\sqrt{\varepsilon_{oh}} + (1-\emptyset_h)[\emptyset_c S_{wc}\sqrt{\varepsilon_{wc}} + \emptyset_c(1-S_{wc})\sqrt{\varepsilon_{oc}} + (1-\emptyset_c)\sqrt{\varepsilon_m}],$$

where $\varepsilon_{CRIM}$ is permittivity of the mixing model, $\emptyset_h$ is porosity of the host fluid, $S_{wh}$ is water saturation of the host fluid, $\varepsilon_{wh}$ is permittivity of the host fluid based on the host fluid being water, $\varepsilon_{oh}$ is the permittivity of the host fluid based on the host fluid being oil, $\emptyset_c$ is porosity of the drill cuttings, $S_{wc}$ is water saturation of the drill cuttings, $\varepsilon_{wc}$ is permittivity of water in pores of the drill cuttings, $\varepsilon_{oc}$ is permittivity of oil in the pores of the drill cuttings, and $\varepsilon_m$ is the permittivity of a solid portion of the drill cuttings.

Embodiment 6

The system as in any prior embodiment, wherein the processor is configured to obtain the permittivity of the host fluid based on the host fluid being water $\varepsilon_{wh}$, the permittivity of the host fluid based on the host fluid being oil $\varepsilon_{oh}$, the permittivity of the water in the pores of the drill cuttings $\varepsilon_{wc}$, the permittivity of the oil in the pores of the drill cuttings $\varepsilon_{oc}$, as known values.

Embodiment 7

The system as in any prior embodiment, wherein the processor is configured to obtain the representation for five different conditions, each of the five different conditions including a different material as the host fluid or a different temperature of the host fluid as compared to any other of the five different conditions.

Embodiment 8

The system as in any prior embodiment, wherein, based on the representation obtained for the five different conditions, the processor is configured to solve for the one or more parameters including the porosity of the host fluid $\emptyset_h$, the water saturation of the host fluid $S_{wh}$, the porosity of the drill cuttings $\emptyset_c$, the water saturation of the drill cuttings $S_{wc}$, and the permittivity of a solid portion of the drill cuttings $\varepsilon_m$.

Embodiment 9

A method of evaluating a formation by analyzing drill cuttings, the method comprising: obtaining, using a multi-frequency dielectric coaxial probe, a reflected voltage from a medium under test based on a reference voltage over a frequency range, the medium under test including the drill cuttings; computing, using a processor, an effective permittivity of the drill cuttings over the frequency range based on a reflection coefficient, which is a ratio of the reflected voltage to the reference voltage over the frequency range; and determining, using the processor, one or more parameters from the effective permittivity, wherein the one or more parameters are used to make decisions about subsequent drilling in the formation.

Embodiment 10

The method as in any prior embodiment, further comprising forming the medium under test to include a host fluid.

Embodiment 11

The method as in any prior embodiment, further comprising determining the effective permittivity over the frequency range, using water as the host fluid, as a first data set, determining the effective permittivity over the frequency range, using oil as the host fluid, as a second data set, determining a difference between a value of the effective permittivity in the first data set and in the second data set at a frequency below a cutoff frequency $f_c$ as $m_{LF}$, and determining a difference between a value of the effective permittivity in the first data set and in the second data set at a frequency above the cutoff frequency $f_c$ as $m_{HF}$.

Embodiment 12

The method as in any prior embodiment, further comprising the processor determining that a film on the drill cuttings is water based on $m_{LF}/m_{HF}$ being ≤1 and determining that the film on the drill cuttings is oil based on $m_{LF}/m_{HF}$ being >>1.

Embodiment 13

The method as in any prior embodiment, further comprising the processor using a complex refractive index model (CRIM) mixing model with the effective permittivity to obtain a representation:

$$\sqrt{\varepsilon_{CRIM}} = \emptyset_h S_{wh}\sqrt{\varepsilon_{wh}} + \emptyset_h(1-S_{wh})\sqrt{\varepsilon_{oh}} + (1-\emptyset_h)[\emptyset_c S_{wc}\sqrt{\varepsilon_{wc}} + \emptyset_c(1-S_{wc})\sqrt{\varepsilon_{oc}} + (1-\emptyset_c)\sqrt{\varepsilon_m}],$$

where $\varepsilon_{CRIM}$ is permittivity of the mixing model, $\emptyset_h$ is porosity of the host fluid, $S_{wh}$ is water saturation of the host fluid, $\varepsilon_{wh}$ is permittivity of the host fluid based on the host fluid being water, $\varepsilon_{oh}$ is the permittivity of the host fluid based on the host fluid being oil, $\emptyset_c$ is porosity of the drill cuttings, $S_{wc}$ is water saturation of the drill cuttings, $\varepsilon_{wc}$ is permittivity of water in pores of the drill cuttings, $\varepsilon_{oc}$ is permittivity of oil in the pores of the drill cuttings, and $\varepsilon_m$ is the permittivity of a solid portion of the drill cuttings.

Embodiment 14

The method as in any prior embodiment, further comprising the processor obtaining the permittivity of the host fluid based on the host fluid being water $\varepsilon_{wh}$, the permittivity of the host fluid based on the host fluid being oil $\varepsilon_{oh}$, the permittivity of the water in the pores of the drill cuttings $\varepsilon_{wc}$, the permittivity of the oil in the pores of the drill cuttings $\varepsilon_{oc}$, as known values.

Embodiment 15

The method as in any prior embodiment, further comprising the processor obtaining the representation for five different conditions, each of the five different conditions including a different material as the host fluid or a different temperature of the host fluid as compared to any other of the five different conditions.

Embodiment 16

The method as in any prior embodiment, further comprising the processor solving, based on the representation obtained for the five different conditions, for the one or more parameters including the porosity of the host fluid $Ø_h$, the water saturation of the host fluid $S_{wh}$, the porosity of the drill cuttings $Ø_c$, the water saturation of the drill cuttings $S_{wc}$, and the permittivity of a solid portion of the drill cuttings $\varepsilon_m$.

Embodiment 17

A resource recovery system, comprising: a drill configured to cut through a formation and generate drill cuttings; a multi-frequency dielectric coaxial probe configured to obtain a reflected voltage from a medium under test based on a reference voltage over a frequency range, the medium under test including the drill cuttings; and a processor configured to compute an effective permittivity of the drill cuttings over the frequency range based on a reflection coefficient, which is a ratio of the reflected voltage to the reference voltage over the frequency range, and to determine one or more parameters from the effective permittivity, wherein the one or more parameters are used to make decisions about subsequent drilling in the formation.

Embodiment 18

The system as in any prior embodiment, wherein the medium under test also includes a host fluid.

Embodiment 19

The system as in prior embodiment, wherein the processor is further configured to determine the effective permittivity over the frequency range, using water as the host fluid, as a first data set, to determine the effective permittivity over the frequency range, using oil as the host fluid, as a second data set, to determine a difference between a value of the effective permittivity in the first data set and in the second data set at a frequency below a cutoff frequency $f_c$ as $m_{LF}$, and to determine a difference between a value of the effective permittivity in the first data set and in the second data set at a frequency above the cutoff frequency $f_c$ as $m_{HF}$.

Embodiment 20

The system as in any prior embodiment, wherein the processor is configured to determine that a film on the drill cuttings is water based on $m_{LF}/m_{HF}$ being $\leq 1$ and to determine that the film on the drill cuttings is oil based on $m_{LF}/m_{HF}$ being $\gg 1$.

The use of the terms "a" and "an" and "the" and similar referents in the context of describing the invention (especially in the context of the following claims) are to be construed to cover both the singular and the plural, unless otherwise indicated herein or clearly contradicted by context. Further, it should be noted that the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

The teachings of the present disclosure may be used in a variety of well operations. These operations may involve using one or more treatment agents to treat a formation, the fluids resident in a formation, a wellbore, and/or equipment in the wellbore, such as production tubing. The treatment agents may be in the form of liquids, gases, solids, semi-solids, and mixtures thereof. Illustrative treatment agents include, but are not limited to, fracturing fluids, acids, steam, water, brine, anti-corrosion agents, cement, permeability modifiers, drilling muds, emulsifiers, demulsifiers, tracers, flow improvers etc. Illustrative well operations include, but are not limited to, hydraulic fracturing, stimulation, tracer injection, cleaning, acidizing, steam injection, water flooding, cementing, etc.

While the invention has been described with reference to an exemplary embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited.

What is claimed is:

1. A system to evaluate a formation by analyzing drill cuttings, the system comprising:
   a multi-frequency dielectric coaxial probe configured to obtain a reflected voltage from a medium under test based on a reference voltage over a frequency range, the medium under test including the drill cuttings; and
   a processor configured to compute an effective permittivity of the drill cuttings over the frequency range based on a reflection coefficient, which is a ratio of the reflected voltage to the reference voltage over the frequency range, and to determine one or more parameters from the effective permittivity, wherein the one or more parameters are used to make decisions about subsequent drilling in the formation.

2. The system according to claim 1, wherein the medium under test also includes a host fluid.

3. The system according to claim 2, wherein the processor is further configured to determine the effective permittivity over the frequency range, using water as the host fluid, as a first data set, to determine the effective permittivity over the frequency range, using oil as the host fluid, as a second data set, to determine a difference between a value of the effective permittivity in the first data set and in the second data set at a frequency below a cutoff frequency $f_c$ as $m_{LF}$, and to determine a difference between a value of the effective permittivity in the first data set and in the second data set at a frequency above the cutoff frequency $f_c$ as $m_{HF}$.

4. The system according to claim 3, wherein the processor is configured to determine that a film on the drill cuttings is water based on $m_{LF}/m_{HF}$ being $\leq 1$ and to determine that the film on the drill cuttings is oil based on $m_{LF}/m_{HF}$ being $\gg 1$.

5. The system according to claim 2, wherein the processor is configured to use a complex refractive index model (CRIM) mixing model with the effective permittivity to obtain a representation:

$$\sqrt{\varepsilon_{CRIM}} = \emptyset_h S_{wh}\sqrt{\varepsilon_{wh}} + \emptyset_h(1-S_{wh})\sqrt{\varepsilon_{oh}} + (1-\emptyset_h)[\emptyset_c S_{wc}\sqrt{\varepsilon_{wc}} + \emptyset_c(1-S_{wc})\sqrt{\varepsilon_{oc}} + (1-\emptyset_c)\sqrt{\varepsilon_m}],$$

where $\varepsilon_{CRIM}$ is permittivity of the mixing model, $\emptyset_h$ is porosity of the host fluid, $S_{wh}$ is water saturation of the host fluid, $\varepsilon_{wh}$ is permittivity of the host fluid based on the host fluid being water, $\varepsilon_{oh}$ is the permittivity of the host fluid based on the host fluid being oil, $\emptyset_c$ is porosity of the drill cuttings, $S_{wc}$ is water saturation of the drill cuttings, $\varepsilon_{wc}$ is permittivity of water in pores of the drill cuttings, $\varepsilon_{oc}$ is permittivity of oil in the pores of the drill cuttings, and $\varepsilon_m$ is the permittivity of a solid portion of the drill cuttings.

6. The system according to claim 5, wherein the processor is configured to obtain the permittivity of the host fluid based on the host fluid being water $\varepsilon_{wh}$, the permittivity of the host fluid based on the host fluid being oil $\varepsilon_{oh}$, the permittivity of the water in the pores of the drill cuttings $\varepsilon_{wc}$, the permittivity of the oil in the pores of the drill cuttings $\varepsilon_{oc}$, as known values.

7. The system according to claim 5, wherein the processor is configured to obtain the representation for five different conditions, each of the five different conditions including a different material as the host fluid or a different temperature of the host fluid as compared to any other of the five different conditions.

8. The system according to claim 7, wherein, based on the representation obtained for the five different conditions, the processor is configured to solve for the one or more parameters including the porosity of the host fluid $\emptyset_h$, the water saturation of the host fluid $S_{wh}$, the porosity of the drill cuttings $\emptyset_c$, the water saturation of the drill cuttings $S_{wc}$, and the permittivity of a solid portion of the drill cuttings $\varepsilon_m$.

9. A method of evaluating a formation by analyzing drill cuttings, the method comprising:
obtaining, using a multi-frequency dielectric coaxial probe, a reflected voltage from a medium under test based on a reference voltage over a frequency range, the medium under test including the drill cuttings;
computing, using a processor, an effective permittivity of the drill cuttings over the frequency range based on a reflection coefficient, which is a ratio of the reflected voltage to the reference voltage over the frequency range; and
determining, using the processor, one or more parameters from the effective permittivity, wherein the one or more parameters are used to make decisions about subsequent drilling in the formation.

10. The method according to claim 9, further comprising forming the medium under test to include a host fluid.

11. The method according to claim 10, further comprising determining the effective permittivity over the frequency range, using water as the host fluid, as a first data set, determining the effective permittivity over the frequency range, using oil as the host fluid, as a second data set, determining a difference between a value of the effective permittivity in the first data set and in the second data set at a frequency below a cutoff frequency $f_c$ as $m_{LF}$, and determining a difference between a value of the effective permittivity in the first data set and in the second data set at a frequency above the cutoff frequency $f_c$ as $m_{HF}$.

12. The method according to claim 11, further comprising the processor determining that a film on the drill cuttings is water based on $m_{LF}/m_{HF}$ being $\leq 1$ and determining that the film on the drill cuttings is oil based on $m_{LF}/m_{HF}$ being $\gg 1$.

13. The method according to claim 10, further comprising the processor using a complex refractive index model (CRIM) mixing model with the effective permittivity to obtain a representation:

$$\sqrt{\varepsilon_{CRIM}} = \emptyset_h S_{wh}\sqrt{\varepsilon_{wh}} + \emptyset_h(1-S_{wh})\sqrt{\varepsilon_{oh}} + (1-\emptyset_h)[\emptyset_c S_{wc}\sqrt{\varepsilon_{wc}} + \emptyset_c(1-S_{wc})\sqrt{\varepsilon_{oc}} + (1-\emptyset_c)\sqrt{\varepsilon_m}],$$

where $\varepsilon_{CRIM}$ is permittivity of the mixing model, $\emptyset_h$ is porosity of the host fluid, $S_{wh}$ is water saturation of the host fluid, $\varepsilon_{wh}$ is permittivity of the host fluid based on the host fluid being water, $\varepsilon_{oh}$ is the permittivity of the host fluid based on the host fluid being oil, $\emptyset_c$ is porosity of the drill cuttings, $S_{wc}$ is water saturation of the drill cuttings, $\varepsilon_{wc}$ is permittivity of water in pores of the drill cuttings, $\varepsilon_{oc}$ is permittivity of oil in the pores of the drill cuttings, and $\varepsilon_m$ is the permittivity of a solid portion of the drill cuttings.

14. The method according to claim 13, further comprising the processor obtaining the permittivity of the host fluid based on the host fluid being water $\varepsilon_{wh}$, the permittivity of the host fluid based on the host fluid being oil $\varepsilon_{oh}$, the permittivity of the water in the pores of the drill cuttings $\varepsilon_{wc}$, the permittivity of the oil in the pores of the drill cuttings $\varepsilon_{oc}$, as known values.

15. The method according to claim 13, further comprising the processor obtaining the representation for five different conditions, each of the five different conditions including a different material as the host fluid or a different temperature of the host fluid as compared to any other of the five different conditions.

16. The method according to claim 15, further comprising the processor solving, based on the representation obtained for the five different conditions, for the one or more parameters including the porosity of the host fluid $\emptyset_h$, the water saturation of the host fluid $S_{wh}$, the porosity of the drill cuttings $\emptyset_c$, the water saturation of the drill cuttings $S_{wc}$, and the permittivity of a solid portion of the drill cuttings $\varepsilon_m$.

17. A resource recovery system, comprising:
a drill configured to cut through a formation and generate drill cuttings;
a multi-frequency dielectric coaxial probe configured to obtain a reflected voltage from a medium under test based on a reference voltage over a frequency range, the medium under test including the drill cuttings; and
a processor configured to compute an effective permittivity of the drill cuttings over the frequency range based on a reflection coefficient, which is a ratio of the reflected voltage to the reference voltage over the frequency range, and to determine one or more parameters from the effective permittivity, wherein the one or more parameters are used to make decisions about subsequent drilling in the formation.

18. The system according to claim 17, wherein the medium under test also includes a host fluid.

19. The system according to claim 18, wherein the processor is further configured to determine the effective permittivity over the frequency range, using water as the host fluid, as a first data set, to determine the effective permittivity over the frequency range, using oil as the host fluid, as a second data set, to determine a difference between a value of the effective permittivity in the first data set and in the second data set at a frequency below a cutoff frequency $f_c$ as $m_{LF}$, and to determine a difference between a value of the effective permittivity in the first data set and in the second data set at a frequency above the cutoff frequency $f_c$ as $m_{HF}$.

20. The system according to claim 19, wherein the processor is configured to determine that a film on the drill cuttings is water based on $m_{LF}/m_{HF}$ being $\leq 1$ and to determine that the film on the drill cuttings is oil based on $m_{LF}/m_{HF}$ being $\gg 1$.

* * * * *